US007015009B2

(12) United States Patent
Christner et al.

(10) Patent No.: US 7,015,009 B2
(45) Date of Patent: Mar. 21, 2006

(54) TEST STRIP FOR DETERMINING DIALYSATE COMPOSITION

(75) Inventors: James E. Christner, Elkhart, IN (US); Linda S. Hout, Edwardsburg, MI (US)

(73) Assignee: Serim Research Corporation, Elkhart, IN (US)

( * ) Notice: Subject to any disclaimer, the term of this patent is extended or adjusted under 35 U.S.C. 154(b) by 486 days.

(21) Appl. No.: 10/195,692

(22) Filed: Jul. 15, 2002

(65) Prior Publication Data

US 2003/0044873 A1 Mar. 6, 2003

Related U.S. Application Data

(63) Continuation-in-part of application No. 09/727,190, filed on Nov. 30, 2000, now Pat. No. 6,444,435.

(51) Int. Cl.
 C12Q 1/54 (2006.01)
(52) U.S. Cl. .......................................... 435/14; 422/56
(58) Field of Classification Search ................ 435/14, 435/4, 287.1, 287.7; 422/55–61; 210/647
 See application file for complete search history.

(56) References Cited

U.S. PATENT DOCUMENTS

| | | | | |
|---|---|---|---|---|
| 2,912,309 | A | 11/1959 | Free ............................. | 23/253 |
| 2,981,606 | A | 4/1961 | Keston ......................... | 23/230 |
| 3,122,420 | A | 2/1964 | Rebar, Jr. et al. ............. | 23/253 |
| 3,232,710 | A | 2/1966 | Rieckmann et al. .......... | 23/253 |
| 4,391,905 | A * | 7/1983 | Bauer .......................... | 435/14 |
| 4,897,184 | A | 1/1990 | Shouldice et al. ............ | 210/87 |
| 5,252,213 | A * | 10/1993 | Ahmad et al. ............... | 210/542 |
| 5,616,248 | A | 4/1997 | Schal .......................... | 210/647 |
| 5,643,452 | A | 7/1997 | Althin et al. ............. | 210/500.23 |
| 5,662,806 | A | 9/1997 | Keshaviah et al. .......... | 210/739 |
| 5,690,831 | A | 11/1997 | Kenley et al. ............... | 210/646 |
| 5,698,090 | A | 12/1997 | Bene et al. ................... | 210/85 |
| 5,705,356 | A * | 1/1998 | De Giorgio .................. | 435/25 |
| 5,711,883 | A | 1/1998 | Folden et al. ............... | 210/646 |
| 5,788,846 | A | 8/1998 | Sternby ....................... | 210/647 |
| 5,811,254 | A | 9/1998 | Wu .............................. | 435/28 |
| 5,888,758 | A | 3/1999 | Wu .............................. | 435/28 |
| 6,027,469 | A | 2/2000 | Johnson ........................ | 604/4 |
| 6,444,435 | B1 * | 9/2002 | Christner et al. ............. | 435/14 |

FOREIGN PATENT DOCUMENTS

| | | |
|---|---|---|
| EP | 0 278 100 | 12/1987 |
| EP | 0 370 850 | 2/1989 |
| EP | 0 505 763 | 2/1992 |
| JP | 49046497 A2 * | 5/1974 |

OTHER PUBLICATIONS

AAMI Standards, vol. 3, Dialysis. Hemodialysis Systems, Assoc for the Advancement of Medcical Instrumentation ANSI/AAMI RD5-1992, 1998.*
CAPLUS abstract (Acc. No. 1974:501579) of JP 49046497 A2. Maekawa et al. (1974). Body Fluid Bicarbonate Determination.
WWW.ROCKWELLMED.COM "Acidified Concentrate Solutionn for Hemodialysis", Rockwell Medical Technologies (Mar. 2, 2000).
John T. Daugirdas and Todd S. Ing."Handbook of Dialysis, 2nd Edition" Rockwell Medical Technologies Inc. Mar. 2000.
WWW.ROCKWELLMED.COM, "Sterilyte Liquid Bicarbonate For Hemodialysis", Rockwell Medical Technologies, Inc. (Mar. 2, 2000).
Association For The Advancement Of Medical Instrumentation, AAMI Standards and Recommended Practices, vol. 3, Dialysis (Mar. 16, 2002).
T.D. Palo, "Chlorine Dioxide: a new agent for dialysis monitor disinfection in a pediatric center", Blood Purif. (Jan. 1, 1997).
W.A. Rutala, "Uses of inorganic hypochlorite (bleach) in health-care facilities", Clinical Microbiology Reviews (Oct. 1, 1997).
National Kidney Foundation, National Kidney Foundation report on dialyzer reuse. Task Form on Reuse of Dialyzers, Council on Dialysis, National Kidney Foundation (Dec. 1, 1997).
N. Tanaka et al., "The Cleaning and Disinfecting of Hemodialysis Equipment Using Electrolyzed Strong Acid Aqueous Solution", Artifical Organs, (Apr. 1, 1999).

* cited by examiner

*Primary Examiner*—Ralph Gitomer
(74) *Attorney, Agent, or Firm*—Baker & Daniels LLP

(57) ABSTRACT

A test strip for confirming a desired proportion of components in dialysate, including a first medium capable of indicating the concentration of bicarbonate ion, and a second medium capable of indicating the concentration of glucose. The test strip defines a first region impregnated with the first medium, and a second region impregnated with the second medium. The test strip optionally includes a third medium capable of indicating the pH of the dialysate. The third medium is impregnated at a third region on the test strip. Alternatively, the test strip comprises a bicarbonate test pad attached to the first region, a glucose test pad attached to the second region, and optionally a pH test pad attached to the third region. The glucose test pad is impregnated with the first medium, the glucose test pad is impregnated with the second medium, and the pH test pad is impregnated with the third medium.

44 Claims, 1 Drawing Sheet

TEST STRIP FOR DETERMINING DIALYSATE COMPOSITION

CROSS REFERENCE TO RELATED APPLICATIONS

This application is a Continuation-in-part of U.S. application Ser. No. 09/727,190, entitled TEST STRIP FOR DETERMINING DIALYSATE COMPOSITION, filed Nov. 30, 2000, and issued as U.S. Pat. No. 6,444,435 on Sep. 3, 2002.

BACKGROUND OF THE INVENTION

1. Field of the Invention

The present invention relates to the testing of dialysates, used in kidney dialysis, to confirm that the dialysates are safe for use to cleanse the blood of patients with kidney failure. More particularly, the present invention relates to devices and methods for confirming that the components of dialysates are present in the correct proportions.

2. Description of the Related Art

Dialysates are used in kidney dialysis (hemodialysis) to cleanse the blood of patients with kidney failure. Generally, dialysate is a solution of buffered salts and glucose in purified water. In the majority of dialysates, a bicarbonate ion is the buffering ion. Bicarbonate dialysate is prepared by combining a bicarbonate concentrate with an acid concentrate, and then diluting the mixture with purified water to obtain the correct proportion of the dialysate components. Clinical technicians may prepare the bicarbonate concentrate "on site" at a dialysis facility, but more commonly, the bicarbonate concentrate is purchased along with the acid concentrate from a commercial supplier.

The dialysate is typically prepared by a dialysis machine, which performs the actual combining, mixing and diluting of the bicarbonate and acid concentrates. Dialysis machines generally include a blood pump, a dialysis solution delivery system, and appropriate safety monitors. There are two major types of dialysis solution delivery systems, a central proportioning delivery system and an individual proportioning system. In the central proportioning delivery system, all of the dialysate is produced by a single machine, and the dialysate is then pumped through pipes to individual dialysis machines. In an individual proportioning delivery system, each dialysis machine proportions the dialysate separately. The blood pump moves the patient's blood to a dialyzer where the blood is cleansed with the dialysate. The cleansed blood is returned to the patient, and the used dialysate flows into a drain and is discarded.

If the proportioning system that dilutes the bicarbonate and acid concentrates with water malfunctions, an excessively dilute or concentrated dialysate may be produced. Daugirdas, J. T., Ing, T. S., Handbook of Dialysis, $2^{nd}$ ed., Little, Brown and Company, Boston/New York/Toronto/London, 1994, p.48. Exposure of blood to a severely hyperosmolar (too concentrated) dialysate can lead to hypernatremia and other electrolyte disturbances, while exposure to a severely hypoosmolar (too dilute) dialysate can result in rapid hemolysis or hyponatremia. Id. It is therefore critical to ensure that the dialysate is proportioned correctly such that it is safe for use with the blood of a patient before dialysis begins. According to the industry standards, the pH of dialysate should be between 6.0 and 8.0. ANSI/AAMI RD5, §3.3.1.6 (1992). Additionally, all solutes identified on a concentrate label should be present within +/−5% of the stated concentration or weight, while sodium and chloride, in particular, should be present within +/−2% of the labeled concentration or weight. ANSI/AAMI RD5, §3.3.1.2 (1992). Generally, the concentration of the ionic components of the dialysate can be indirectly determined by the electrical conductivity of the dialysate, because the primary solutes in dialysates are electrolytes.

Most dialysis machines are equipped with built-in meters or other safety devices that continuously monitor, among other variables, dialysate concentration and pH. The pH of the dialysate is typically measured by means of a glass pH electrode built into the dialysis system. The dialysate concentration is typically determined indirectly by measuring the electrical conductivity of the dialysate with a conductivity meter.

One problem with these safety devices is that both the conductivity meters and the glass pH electrodes require routine maintenance and calibration checks to insure proper operation. Disadvantageously, this maintenance and calibration checks are time consuming, and are often beyond the technical capability of clinic personnel.

Further disadvantages result from the nature of the conductivity and pH measurements. Specifically, because conductivity is a measurement of the total ion concentration in solution, it is therefore a nonspecific measurement of the concentrations of particular ionic components in the dialysate. This nonspecific measurement can fail because both the bicarbonate concentrate and acid concentrate each contain specific ionic components. In some cases, the observed conductivity measurements are correct, when in fact, the proportion of the bicarbonate and acid concentrates is incorrect. For example, if the concentration of one of the concentrates is too high and the other is too low, the concentrate whose concentration is too high will compensate for the concentrate whose concentration is too low. This results in a conductivity measurement that is mistakenly observed as an indication that the dialysate composition is correct. This problem is recognized in the above-referenced ANSI/AAMI standard, which states:

Adequate monitoring does not currently exist to assure that mismatched concentrates will not produce a final dialysate of proper total conductivity but improper composition. The user is cautioned not to rely solely on conductivity measurements to ensure safety, but to consider all relevant factors, including pH.

ANSI/AAMI RD5, §3.3.1.6 (1992) (emphasis in original). Another concern with the current systems is that pH measurements are also by nature, as logarithmic measurements, insensitive to errors in the proportion of the bicarbonate and acid concentrates in the dialysate. Only substantial changes in the proportion of the bicarbonate and acid concentrates will affect the change of the pH value. For example, at the correct proportion of the bicarbonate and acid concentrates, the calculated pH is 7.6. However, if the amount of acid concentrate is doubled, the pH will drop slightly to 7.3, which is well within the acceptable pH range of 6.0 to 8.0, even though the actual proportion of bicarbonate and acid concentrates is incorrect.

An alternative device for measuring the pH of a solution has been in a form of test strips. Such test strips have been disclosed in the U.S. Pat. No. 3,122,420 issued to Rebar et al. in 1964, and the U.S. Pat. No. 3,232,710, issued to Reickmann et al., in 1966. The '420 patent discloses bibulous paper strips impregnated with a diagnostic composition for use in determining the hydrogen ion concentration of biological fluids such as human urine. The '710 patent, in addition to the pH test paper strips, discloses glucose test paper strips, albumin test paper strips, and multiple test strips. Another glucose test strip appropriate for the detection of glucose in body fluids such as urine has also been disclosed in the U.S. Pat. No. 2,912,309, issued to Free, in 1959.

Despite the different kinds of test strips listed above, there has not been a test strip that can be used in determining the proportion of bicarbonate and acid concentrates in dialysate.

What is needed is a test for determining whether the bicarbonate and acid concentrates in dialysate are present in the correct proportion.

What is also needed is a test that will enable users to obtain a quick, reliable, and visual qualitative determination of whether bicarbonate and acid concentrates are correctly proportioned in dialysate.

A further need is for tests that may be performed by clinical personnel who do not possess advanced scientific and/or technical training.

SUMMARY OF THE INVENTION

The present invention contemplates test strips and methods for confirming the composition of dialysate, which is the product of mixing the correct proportion of bicarbonate concentrate with acid concentrate and purified water. The proportion of bicarbonate concentrate is determined by a direct measurement of bicarbonate ion concentration, and the proportion of acid concentrate is determined by a direct measurement of glucose concentration. The bicarbonate ion is a suitable marker for bicarbonate concentrate because it is a major component of the bicarbonate concentrate that is not present in the acid concentrate. Likewise, glucose is a suitable marker for acid concentrate because it is a major component of the acid concentrate that is not present in the bicarbonate concentrate. If the concentration of each measured component is in the correct range, then the proportion of the concentrates in the dialysate is in an acceptable range.

The test strips contain multiple test media for facilitating the determination of bicarbonate ion and glucose concentration. In one embodiment, the test strip comprises a first medium capable of indicating the concentration of bicarbonate ion, and a second medium capable of indicating the concentration of glucose in the dialysate. Optionally, the test strip further comprises a third medium capable of indicating the pH of the dialysate.

In an exemplary embodiment, the test strip defines a first region that is impregnated with a first medium, and a second region that is impregnated with a second medium. In addition, the test strip optionally defines a third region that is impregnated with a third medium. Preferably, the test strip is made of an absorbent material that is compatible with the three media.

In another exemplary embodiment, the test strip comprises a bicarbonate test pad that has been impregnated with the first medium, a glucose test pad that has been impregnated with the second medium, and optionally a pH test pad that has been impregnated with the third medium. The test pads preferably are made of an absorbent material that is compatible with the three media. In addition, the test strip further comprises a backing material to which the pads are mounted thereon. It is not critical in which order the pads are disposed on the test strip. It is preferable, however, that the pads are attached toward one end of the backing material, leaving the other end accessible for handling.

Any suitable media are contemplated so long as they indicate the relative proportions of glucose and bicarbonate ion. Most preferably, the media include a chromogenic indicator that provides a color change upon a chemical reaction.

The present invention also provides methods for confirming that the dialysate contains the desired proportion of bicarbonate ion and glucose. The methods of this invention are simple to perform, safe and effective. In accordance with one embodiment, the method includes the steps of providing a test strip of this invention, exposing the test strip to the dialysate that has been prepared preferably by the dialysis machine, and inspecting the test strip for an indication of the concentration of bicarbonate ion, an indication of the concentration of glucose, and optionally, the pH of the dialysate.

One advantage of the present invention is that the measurement of a specific marker component from each of the bicarbonate concentrate and the acid concentrate results in an accurate and direct determination of the proportion of the bicarbonate concentrate and the acid concentrate in the dialysate.

Another advantage of the tests of this invention is that they are easy to use and to interpret.

Still another advantage of this invention is that it allows a user who does not possess advanced scientific and/or technical training to obtain a quick and reliable visual confirmation of whether the bicarbonate and acid concentrates are present in the correct proportion in dialysate.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying figures, wherein.

Although the drawings represent embodiments of the present invention, the drawings are not necessarily to scale and certain features may be exaggerated in order to better illustrate and explain the present invention. The exemplification set out herein illustrates an embodiment of the invention, in one form, and such exemplifications are not to be construed as limiting the scope of the invention in any manner.

DETAILED DESCRIPTION

The embodiments disclosed below are not intended to be exhaustive or limit the invention to the precise forms disclosed in the following detailed description. Rather, the embodiments are chosen and described so that others skilled in the art may utilize their teachings.

The present invention provides an apparatus and method for checking dialysate makeup by measuring at least one ingredient from each of the bicarbonate concentrate and acid concentrate of the dialysate. If both are in the correct range, then the proportions of all three components, namely, the bicarbonate concentrate, the acid concentrate, and water must be in the acceptable range. The bicarbonate ion is derived only from the bicarbonate concentrate and thus can be used as the marker for bicarbonate concentrate. Of the number of ingredients unique to the acid concentrate, glucose is the most suitable marker because it is present at a consistent level in almost all dialysates.

In accordance with the present invention as shown in FIGS. 1–4, the test strip for confirming the desired proportion of bicarbonate and acid concentrates in dialysate comprises a first medium capable of indicating the concentration of bicarbonate ion, and a second medium capable of indicating the concentration of glucose in the dialysate. Further, the test strip optionally comprises a third medium capable of indicating the pH of the dialysate. The test strip can be made of any suitable bibulous carriers, such as filter paper, or sponges. Additionally, other materials such as beaded columns or wooden sticks are contemplated.

Figure 1:
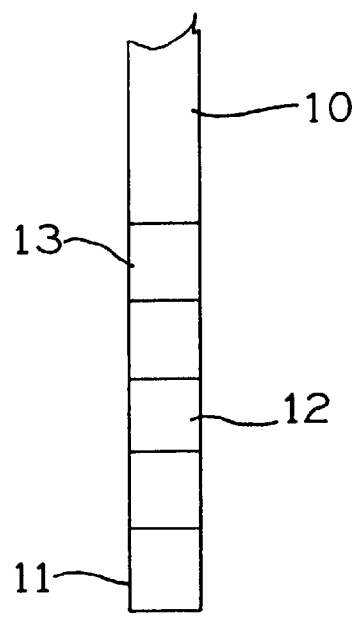
FIG. 1 is a front elevational view of a test strip in accordance with one embodiment of the present invention.
Figure 2:
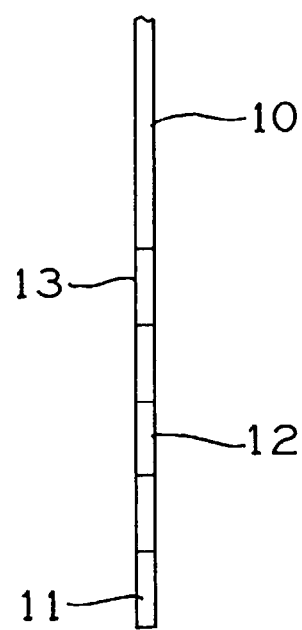
FIG. 2 is a side elevational view of the test strip of FIG. 1.

In an exemplary embodiment shown in FIGS. 1–2, test strip 10 includes a first medium impregnated thereon at a first region 11, and a second medium impregnated thereon at a second region 12. Test strip 10 optionally includes a third medium impregnated thereon at a third region 13. The third medium is capable of indicating the pH of the dialysate. The pH determination is used as an additional test to confirm whether the concentrates are in the right proportion. It is not critical how the regions are arranged on the test strip.

Figure 3:
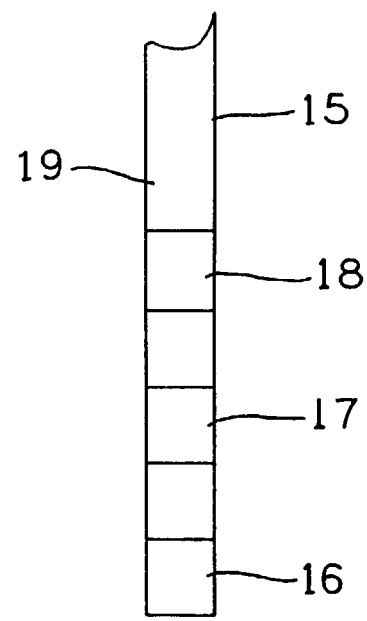
FIG. 3 is a front elevational view of another test strip in accordance with another embodiment of the present invention.
Figure 4:
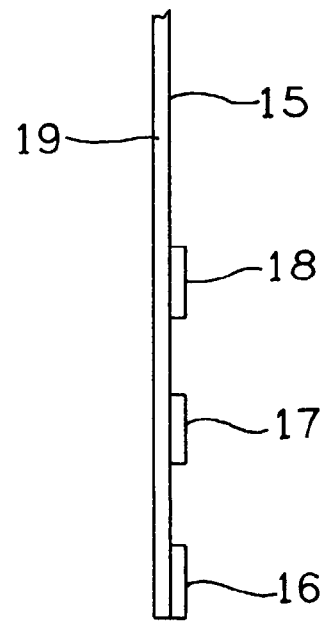
FIG. 4 is a side elevational view of the test strip of FIG. 3.

In another embodiment shown in FIGS. 3–4, test strip 15 includes a bicarbonate test pad localized at a first region 16, a glucose test pad localized at a second region 17, and optionally, a pH test pad localized at a third region 18. Each region may be disposed in any order from an end of test strip 15. The bicarbonate test pad is impregnated with the first medium capable of indicating bicarbonate ion concentration, the glucose test pad is impregnated with the second medium capable of indicating glucose concentration, and the pH test pad is impregnated with the third medium capable of indicating the pH of the dialysate. Exemplarily, the test strip 15 includes a backing material 19. The backing material can be made of any suitable materials, such as plastic, poly-styrene, paper, wood, or glass.

In the exemplary embodiments, each medium is prepared following the concepts and procedures described herein below.

Bicarbonate Concentration

The concentration of bicarbonate ion in a dialysate sample is determined by measuring the buffering capacity of the bicarbonate concentrate on a bicarbonate test pad impregnated with the first medium. The first medium includes an acid and a chromogenic pH indicator. During the bicarbonate measurement, the acid in the test pad reacts with the bicarbonate in the dialysate sample. The chemical reaction ultimately alters the pH of the pH indicator within the test pad. The pH indicator is a substance capable of exhibiting a color change responsive to pH changes. The final color of the indicator is matched with a corresponding color on a standard color chart that shows the corresponding pH value. The higher the pH value indicates the higher concentration of the bicarbonate in the dialysate sample. For example, when sodium bicarbonate is present in the dialysate sample, the following reaction (I) occurs within the bicarbonate test pad:

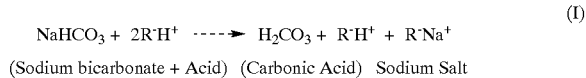

$$NaHCO_3 + 2R^-H^+ \longrightarrow H_2CO_3 + R^-H^+ + R^-Na^+ \quad (I)$$

(Sodium bicarbonate + Acid) (Carbonic Acid) Sodium Salt

The acid within the bicarbonate test pad reacts with sodium bicarbonate and forms carbonic acid. In addition, a ratio of $R^-H^+/R^-Na^+$ is generated in the test pad, at the completion of the reaction. This ratio is determined by the amount of sodium bicarbonate originally present in the test sample. In turn, the $R^-H^+/R^-Na^+$ determines the test pad pH, which can be measured by means of a chromogenic pH indicator. The color of the pH indicator changes with its pH.

Suitable acids that can be used in the bicarbonate test pad are acids having a pKa value of about one unit below that of the bicarbonate ion (pKa=6.4). Acids having pKa values of more than one unit below or less than one unit below that of the bicarbonate ion can also be used. However, the use of the acids having very low pKa value may not be feasible due to the lack of suitable pH indicators. In addition, since a dry medium is preferred, the acid must be a nonvolatile solid. Also, to allow for short reaction times, the acid should be water-soluble. Examples of suitable acids are listed in TABLE 1. The pKa values of these acids are within the desired range of between 2.9 and 5.6. *Lange's Handbook of Chemistry*, 14th Ed., McGraw-Hill, Inc., New York (1992). The invention also contemplates any suitable acid.

TABLE 1

Examples of suitable acids

| Acid | pKa |
| --- | --- |
| Citric acid | 3.1; 4.7 and 5.4 |
| Succinic acid | 4.2 and 5.6 |
| Tartaric acid | 2.9 and 4.2 |
| Phthalic acid | 3.0 and 5.4 |
| Fumaric acid | 3.1 and 4.6 |
| Gluconic acid | 3.9 |

The chromogenic pH indicator is capable of exhibiting a color change when its pH changes. Suitable pH indicators for a bicarbonate test pad should have a pKa value in the same range as that of suitable acids. An indicator with a pKa value in the same range as that of the bicarbonate ion may also be used, but the results may be less predictable since the buffering capacity will vary with bicarbonate concentration. The pKa values of suitable pH indicators (TABLE 2) range from 3.8 to 7.6. *Merck Index*, 10th Edition, Merck & Co., Inc. (1983). It is contemplated that other pH indicators having pKa values slightly below or above the above range may also be used.

TABLE 2

Examples of suitable pH indicators

| Indicator | pKa | Color change Low Bicarbonate ----------> High | |
| --- | --- | --- | --- |
| Bromophenol blue | 3.8 | Yellow | Blue |
| Methyl orange | 3.8 | Red | Yellow |
| Tetrabromophenol blue | 3.8 | Yellow | Blue |
| Congo red | 4.0 | Blue | Red |
| Bromocresol green | 4.6 | Yellow | Blue |

TABLE 2-continued

Examples of suitable pH indicators

| Indicator | pKa | Color change Low Bicarbonate ----------> High | |
|---|---|---|---|
| Litmus | 6.5 | Red | Blue |
| Phenol red | 7.6 | Yellow | Red |

Generally, the bicarbonate test pad should have a broad range of sensitivity because it is desirable to be able to detect a broad range of bicarbonate concentrations in dialysate samples. Particularly, the test should be sensitive enough to detect the bicarbonate concentration in dialysates made from mixing commercial bicarbonate and acid concentrates. It is contemplated that the test is sensitive enough to determine bicarbonate concentration in dialysates prepared by any dialysis machine. The target or the proper dialysate produced by any of the three main types of dialysis machines: 1/36.83 Proportioning System (Drake, Gambro, Baxter, Althin, Braun), 1/35 Proportioning System (Fresenius), and 1/45 Proportioning System (Cobe Machines) contains bicarbonate ion concentration of about 37±2 mEq/L. Of course, it is not possible to estimate the range of concentrations that might result from errors in the bicarbonate concentrate preparation or machine function. Ideally, the test would be able to detect small dialysate deviations arising from these errors. A possible range of incorrect concentrations derived from using a wrong concentration of bicarbonate concentrate and/or acid concentrate with a wrong machine is calculated in the range of 21.4 to 49.7 mEq/L. Also, the test should clearly indicate the situation in which the bicarbonate is very high (about 1200 to 1655 mEq/L in the concentrate) or is missing entirely.

Glucose Concentration

The determination of glucose concentration in a dialysate sample is based on reactions (II) and (III) shown below. The first reaction utilizes an enzyme, glucose oxidase (EC 1.1.3.4), to catalyze oxidization of glucose by atmospheric oxygen to form hydrogen peroxide. The second reaction utilizes an enzyme, horseradish peroxidase (EC 1.11.1.7), to catalyze oxidization of a chromogenic oxidation/reduction indicator by hydrogen peroxide.

$$Glucose + O_2 \rightarrow Gluconic\ Acid + H_2O_2 \qquad (II)$$

(reaction catalyzed by glucose oxidase)

$$H_2O_2 + Reduced\ Indicator \rightarrow Oxidized\ Indicator + H_2O \qquad (III)$$

(reaction catalyzed by horseradish peroxidase)

The chromogenic oxidation/reduction indicator is a substance which, after being oxidized or reduced by hydrogen peroxide, is capable of forming a color different from its original color. The degree of color change depends on the amount of hydrogen peroxide generated, which, in turn, depends on the amount of starting glucose. Therefore, if glucose is present in the dialysate, the color of the indicator in the glucose test pad will change depending on the concentration of the glucose. The final color of the test pad is matched with a corresponding color on a standard chart to indicate a corresponding concentration of glucose.

In the exemplary embodiments, the glucose oxidase enzyme is derived from a microbial source such as *Aspergillus niger* or *Penicillium reticulosum*. However, glucose oxidase from other sources may also be applicable as long as it catalyzes the transition of glucose with the concomitant production of hydrogen peroxide.

Horseradish peroxidase is used in the exemplary embodiments as the catalytic enzyme for the second reaction, however, peroxidase from other sources or any other suitable enzyme is also contemplated.

Examples of suitable oxidation/reduction indicators are presented in TABLE 3. Conyers, S. M., and Kidwell, D. A., *Analyt. Biochem.* 192 (1991) or Blake, D. A. and McLean, N. V., *Analyt. Biochern* 177 (1989). It is contemplated that other substances which exhibit a color change upon reaction with hydrogen peroxide may also be applicable.

TABLE 3

Examples of suitable oxidation/reduction indicators

| Indicator | Maximum Absorbance (nm) | Color |
|---|---|---|
| o-Dianisidine | 460 | Yellow |
| 4-AAP/phenol | 505 | Red/Yellow |
| MBTH/3-dimethylaminobenzoic acid | 590 | Red |
| Tetramethyl benzidine | 650 | Blue |
| Potassium iodide | 352 | Yellow/Brown |

It is also possible that the glucose test pad may be treated with an inert dye of a particular color such as yellow or blue, so that the color change exhibited by the oxidation/reduction indicator is blended with the background color to produce varying tints which correspond to different concentrations of glucose present in the dialysate being tested.

In the exemplary embodiments, the glucose test pad has a broad range of sensitivity. Generally, the glucose test pad would be able to detect the glucose concentration in various dialysate samples. Particularly, the test pad should detect the glucose concentration in dialysates made from commercial concentrates or by dialysis machines. The target dialysate produced by any of the three main types of dialysis machines: 1/36.83 Proportioning System (Drake, Gambro, Baxter, Althin, Braun), 1/35 Proportioning System (Fresenius), and 1/45 Proportioning System (Cobe Machines) contains a glucose concentration of 2 g/L. Of course, it is not possible to estimate the range of concentrations that might result from errors in machine function. Ideally, the test would be able to detect small dialysate deviations arising from these errors. A possible range of incorrect concentrations of glucose derived from using a wrong concentration of bicarbonate concentrate and/or acid concentrate with a wrong machine is in the range of 1.55 to 2.57 g/L. Also, it should clearly indicate instances where glucose is well above normal (about 70 to 90 g/L) in the concentrate or is missing entirely.

pH

The acceptable pH range for the dialysates is 6.0 to 8.0 (ANSI/AAMI RD5-1992, paragraph 3.3.1.6.). The pH of dialysates may be determined by means of a standard pH indicator. However, ideally, the pKa of the pH indicator should be about 7.0. In the exemplary embodiments, the test for pH of dialysates makes use of the Serim Bicarb pH Test Strip (Serim Research Corp., Elkhart, Ind.), which has the applicable sensitivity range. Examples of suitable pH indicators (*Merck Index*, 10th Edition, Merck & Co., Inc. (1983), pp. MISC. 104–105) are listed below in TABLE 4.

TABLE 4

Examples of suitable pH indicators

| Indicator | pKa | Color Change Low pH ----------> High pH |
|---|---|---|
| Bromothymol blue | 6.8 | Yellow ----------> Blue |
| Pyrocatechol violet | 7.0 | Yellow ----------> Violet |
| Tetra-bromophenol sulfonephthalein | 7.4 | Yellow ----------> Purple |
| Neutral red | 7.4 | Red ----------> Yellow |
| Phenol red | 7.6 | Yellow ----------> Red |
| Cresol red | 7.9 | Yellow/red ----------> Purple |

EXAMPLE 1

Preparation of the Bicarbonate Test Pad

The first medium containing at least one acid, at least one pH indicator, and water is prepared as one of the formulations listed herein below. The first medium may include salts and other inert reagents. It is to be understood that these formulations have been chosen as illustrative of the present invention and it will, of course, be apparent to those skilled in the art that various modifications may be made without departing from the spirit and the scope of the present invention.

Formulation 1

| Ingredient | Amount |
|---|---|
| Citric Acid | 0.02 g |
| Sodium Citrate | 0.035 g |
| Nitrazine Yellow | 0.01 g (Inert background colorant) |
| Bromocresol Green | 0.02 g |
| Water | 100 mL |

Hydrochloric acid was added to the above mixture until the pH, as monitored with a glass pH electrode, reached a value of 2.6.

Formulation 2 (Varying the Acid Content of the Test Pad)

| Ingredient | Amount |
|---|---|
| Citric Acid | 0.04 g |
| Sodium Citrate | 0.07 g |
| Nitrazine Yellow | 0.01 g (Inert background colorant) |
| Bromocresol Green | 0.02 g |
| Water | 100 mL |

Hydrochloric acid was added to the above mixture until the pH, as monitored with a glass pH electrode, reached a value of 2.6.

Formulation 3 (Varying the Acid Content of the Test Pad)

| Ingredient | Amount |
|---|---|
| Citric Acid | 0.08 g |
| Sodium Citrate | 0.14 g |
| Nitrazine Yellow | 0.01 g (Inert background colorant) |
| Bromocresol Green | 0.02 g |
| Water | 100 mL |

Hydrochloric acid was added to the above mixture until the pH, as monitored with a glass pH electrode, reached a value of 2.6.

Formulation 4 (Varying the Acid Content of the Test Pad)

| Ingredient | Amount |
|---|---|
| Citric Acid | 0.30 g |
| Sodium Citrate | None |
| Nitrazine Yellow | 0.01 g (Inert background colorant) |
| Bromocresol Green | 0.02 g |
| Water | 100 mL |

Hydrochloric acid was added to the above mixture until the pH, as monitored with a glass pH electrode, reached a value of 2.6.

Formulation 5 (Varying the Acid Content of the Test Pad)

| Ingredient | Amount |
|---|---|
| Citric Acid | 0.45 g |
| Sodium Citrate | None |
| Nitrazine Yellow | 0.01 g (Inert background colorant) |
| Bromocresol Green | 0.02 g |
| Water | 100 mL |

Hydrochloric acid was added to the above mixture until the pH, as monitored with a glass pH electrode, reached a value of 2.6.

Formulation 6 (Varying the Indicator and the pH of the Formula)

| Ingredient | Amount |
|---|---|
| Citric Acid | 0.08 g |
| Sodium Citrate | 0.14 g |
| Nitrazine Yellow | 0.02 g |
| Bromocresol Green | 0.02 g |
| Water | 100 mL |

Hydrochloric acid was added to the above mixture until the pH, as monitored with a glass pH electrode, reached a value of 6.0.

Formulation 7 (Varying the Indicator and the pH of the Formula)

| Ingredient | Amount |
|---|---|
| Citric Acid | 0.08 g |
| Sodium Citrate | 0.14 g |
| Phenol Red | 0.02 g |
| Water | 100 mL |

Hydrochloric acid was added to the above mixture until the pH, as monitored with a glass pH electrode, reached a value of 6.0.

Pieces of filter paper were saturated with the first medium and then dried in a forced-air oven at 60° C. for 10 minutes. The dried pads were then used to prepare test strips. The test strips consist of a 3.25×0.2 inch strip of backing material such as polystyrene, and a 0.2×0.2 inch bicarbonate test pad attached at one end by means of double-sided adhesive tape.

Test of Bicarbonate Test Pad

In order to determine the effectiveness of the test pads made with different formulations, the test strips were dipped in the individual dialysate samples containing 0.5X, 1X and 2X concentrations of bicarbonate, where X=37±2 mEq/L. After two seconds, the strips were removed from the dialysates. The color of each test pad was allowed to develop for about one minute. The results in Table 5 show that the color of the test pads made with Formulations 1–5 changes from yellow to green to blue with the increased bicarbonate concentration. Formulation 5 gives the best color spread and allows the detection of small deviations of bicarbonate concentration. Formulations 1–4 also give similar results. The test pads made from Formulations 6 and 7 exhibited color changes from yellow to orange or red with the increased bicarbonate concentration, and also give good color spreads.

TABLE 5

Result of the testing of bicarbonate test pads

| Bicarbonate test pad | Bicarbonate concentration | Pad color |
|---|---|---|
| Formulation 1–5 | 0.5X | Yellow |
| | 1X | Green |
| | 2X | Blue |
| Formulation 6–7 | 0.5X | Yellow |
| | 1X | Orange |
| | 2X | Red |

EXAMPLE 2

Preparation of a Glucose Test Pad

The second medium contains glucose oxidase, peroxidase, a chromogenic oxidation/reduction indicator, and water. In addition, acids, salts, and inert ingredients may be added. The second medium can be prepared by following Formulation 8:

Formulation 8

| Ingredient | Amount |
|---|---|
| Citric Acid | 0.38 g |
| FD&C Blue | 0.02 g (Inert background color) |
| Sodium Citrate | 5.29 g |
| Polyvinyl pyrrolidone | 0.50 g |
| Potassium iodide | 1.00 g |
| Glucose oxidase | 0.30 g |
| Peroxidase | 0.70 g |
| Water | 100 mL |

It is to be understood that the aforementioned formulation has been chosen as illustrative of the present invention and it will, of course, be apparent to those skilled in the art that various modifications may be made without departing from the spirit and the scope of the present invention. For example, other suitable oxidation/reduction indicators as listed in TABLE 3 may be used in place of potassium iodide.

To prepare the glucose test pad, pieces of filter paper were saturated with the solution of formulation 8 and then dried in a forced-air oven at 55° C. for 10 minutes. The dried pads were then used to prepare test strips. The test strips included a 3.25×0.2 inch polystyrene strip as a backing material, and a 0.2×0.2 inch glucose test pad was attached at one end by means of double-sided adhesive tape.

Test of Glucose Test Pad

To determine the effectiveness of the glucose test pad in measuring glucose concentration in dialysate samples, the glucose test strip was dipped into the dialysate samples containing 1.0, 2.0 and 4.0 g/L glucose for one second. The strip was then removed from the samples and the change in color of the glucose test pad was observed. The color of the pad changed from the original shade of yellow/brown to a fully developed color of a different shade in about two minutes. The results shown in TABLE 6 indicate that a glucose concentration between 1.0 and 4.0 g/L in dialysate samples is readily distinguishable. The 1.0 g/L glucose concentration is representative of a low glucose concentration, 2.0 g/L is the expected glucose concentration in standard dialysates, whereas 4.0 g/L is representative of a high glucose concentration.

TABLE 6

Result of the test of glucose test pad

| Glucose Concentration (g/L) | Final Color of Glucose Test Pad |
|---|---|
| 1.0 (low concentration) | Yellow |
| 2.0 (standard concentration) | Blue/Green |
| 4.0 (high concentration) | Blue |

EXAMPLE 3

Preparation of Test Strips Having Multiple Test Pads

The first medium is prepared as Solution 1, the second medium is prepared as Solution 2, and the third medium is prepared as Solution 3 as listed below. Pieces of filter paper were respectively saturated with each of the three Solutions 1–3 and then dried for 15 minutes in a forced-air oven at 60° C. The dried papers were processed to yield 0.2"×0.2" pads. Two or three pads, one made with each solution, were attached to one end of a 0.2"×3.25" strip of backing material by means of double-sided adhesive tape.

Solution 1. (Bicarbonate Test)

| Ingredient | Amount |
|---|---|
| Citric acid | 0.08 g. |
| Sodium citrate | 0.14 g |
| Nitrazine yellow | 0.01 g |
| Bromocresol green | 0.02 g |
| Water | 100 mL |
| pH adjusted to 2.6 | |

Solution 2. (Glucose Test)

| Citric acid | 0.19 g |
| FD&C blue | 0.01 g |
| Sodium citrate | 2.645 g |

-continued

| | |
|---|---|
| Polyvinyl pyrrolidone | 0.25 g |
| Potassium iodide | 0.50 g |
| Glucose oxidase | 0.1975 g |
| Peroxidase | 0.3718 g |
| Water | 50 mL |

Solution 3. (pH Test)

| | |
|---|---|
| m-cresol purple | 0.072 g |
| 3,4,5,6-TBPS | 0.09 g |
| Water | 50 mL |
| Reagent alcohol | 50 mL |
| pH adjusted to 7.5 | |

It is to be understood that the above solutions have been chosen as illustrative of the present invention and it will of course be apparent to those skilled in the art that various modifications may be made without departing from the spirit and the scope of the present invention. For example, Solution 1 may be made by replacing bromocresol green with any of the pH indicators listed in TABLE 4. Solution 2 may contain, instead of potassium iodide, any of the suitable color indicators listed in TABLE 3. Solution 3 may be replaced by any of the formulations listed in EXAMPLE 1.

Determination of Dialysate Compositions using a Three-test Strip

In order to test whether the three-test strip prepared as described above is effective in determining glucose concentration, bicarbonate concentration, and pH of dialysates, dialysate samples were prepared by mixing known amounts of commercially available acid and bicarbonate concentrates. Five sets of samples designated "low glucose-low bicarbonate", "target", "high glucose-high bicarbonate", "low glucose-high bicarbonate", and "high glucose-low carbonate" were prepared (TABLE 7). The term "low" in the above designations indicates that only half of the correct amount of the concentrate was present, and the term "high" indicates that twice the correct amount of the concentrate was present. The term "target" indicates that the correct amounts of both acid and bicarbonate concentrates were present, wherein the concentration of bicarbonate is 37±2 mEq/L, and the concentration of glucose is 2.0 g/L. The three-test strips were prepared according to EXAMPLES 1 and 2, and were dipped into the dialysate samples for one second. At 10 seconds after removing the strip from the sample, the color of the pH pad was compared to a standard color chart (*Serim. Bicarb pH Test Strips Chart*, Serim Research Corp., Elkhart, Ind.). At 15 seconds, the color of the glucose pad is compared to a corresponding color chart (*The Screen Tint Selector*, published by Moosberg and Company, 301 East Sample Street, South Bend, Ind. 46624), and at 30 seconds, the color of the bicarbonate pad is compared to a corresponding color chart. (*The Screen Tint Selector*, published by Moosberg and Company, 301 East Sample Street, South Bend, Ind. 46624). It should be noted that the reading time may vary depending on the composition of the solutions used to make the individual test pads.

The results summarized in TABLE 7 show that the three-test strips are effective in detecting different compositions of bicarbonate and acid concentrates in the dialysate samples. The final colors of the three test pads on each test strip indicate the bicarbonate concentration, the pH of the solution, and the glucose concentration. As expected, the solution having a "target" composition shows the bicarbonate concentration to be at target and the glucose concentration at 2.0 g/L, with the pH of the solution at 7.0. The pH of the "target" solution, as determined by the pH pad, confirms the correct composition of the bicarbonate and acid concentrates.

The dialysate with low acid concentrate and low bicarbonate concentrate shows a low bicarbonate concentration as read by the bicarbonate test pad, a pH of 7.0 as read by the pH test pad, and a low glucose concentration of 1.0 g/L. The dialysate with high acid concentrate and high bicarbonate concentrate shows a high bicarbonate concentration as read by the bicarbonate test pad, a high pH of 7.4 as read by the pH test pad, and a high glucose concentration of 3.5 g/L. The dialysate with low acid concentrate and high bicarbonate concentrate shows a high bicarbonate concentration as read by the bicarbonate test pad, a high pH of 8.5 as read by the pH test pad, and a low glucose concentration of 1.0 g/L. The dialysate with high acid concentrate and low bicarbonate concentrate shows a low bicarbonate concentration as read by the bicarbonate test pad, a low pH of 6.5 as read by the pH test pad, and a high glucose concentration of 3.5 g/L.

It is to be noted that when both the acid and bicarbonate concentrates are either high or low, the pH value changes very little. However, the glucose and bicarbonate pads clearly indicate a deviation from the correct concentration in all four incorrect solutions.

TABLE 7

Results of dialysate test using three-test strips

| Concentrate Levels in Dialysates | pH Test Pad Result (pH) | Bicarbonate Test Pad Result | Glucose Test Pad Result (g/L) |
|---|---|---|---|
| Target | 7.0 | Target (Green) | 2.0 (target) |
| Low acid and Low Bicarbonate | 7.0 | Low (Yellow) | 1.0 |
| High acid and High Bicarbonate | 7.4 | High (Blue-Green) | 3.5 |
| Low acid and High Bicarbonate | 8.5 | High (Blue-Green) | 1.0 |
| High acid and Low Bicarbonate | 6.5 | Low (Yellow) | 3.5 |

It should be noted, however, that a test strip may be prepared in accordance with EXAMPLE 2 including only bicarbonate and acid test pads, which test strip would indicate the results set forth in TABLE 7 with respect to the bicarbonate and acid concentrate levels. Therefore, a test strip including only bicarbonate and acid test pads may be used to determine whether a dialysate sample includes the correct proportions of bicarbonate and acid concentrates. In this regard, the presence of a pH test pad is optional, wherein the pH test pad result serves to confirm the indications provided by the bicarbonate and acid test pads.

The examples described herein above demonstrate the procedures for making and using test strips for verifying the proportion of bicarbonate and acid concentrates in dialysate. The examples describe several formulations that can be used as the first medium for indicating bicarbonate ion concentration, representing the proportion of the bicarbonate concentrate in the dialysate. The examples further describe a formulation that can be used as the second medium for indicating the concentration of glucose, representing the proportion of the acid concentrate in the dialysate. In accordance with the present invention, there is a possibility of using alternative formulations or ingredients in the production of the test strips. This possibility is advantageous, especially where the availability or the cost of certain ingredient is limiting.

In addition to the bicarbonate ion and glucose concentration, the test strip, in accordance with the present invention, further includes a third medium capable of indicating the pH of the dialysate. The pH measurement is used as an additional test that confirms whether the proportion of the concentrates in the final dialysate is correct.

Based on the above examples, it is clear that the test strips and the methods disclosed herein can be used to accurately and reliably confirm the target proportion of the bicarbonate and the acid concentrates. This confirmation is necessary to ensure that the proper composition of the dialysate is being used to treat the patient effectively and safely. The present invention has several advantages over the standard method of monitoring the conductivity or the pH of the dialysate to ensure the correct proportion of the bicarbonate and acid concentrates. One advantage is that the need for calibrating the conductivity monitor or pH monitor can be eliminated. Another advantage is that this invention allows a user who does not possess advanced technical training to obtain a quick and reliable visual confirmation of whether the bicarbonate and acid concentrates are present in the correct proportion in the dialysate. Finally, the tests of this invention are easy to use and interpret.

Although several broad examples which incorporate the present invention have been described above, it is to be understood that the present invention is not to be limited by the examples disclosed herein. Indeed, the disclosure and examples above teach one of ordinary skill a virtually limitless number of conditions which would be within the scope of the claims appended hereto.

Further, while this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A test strip for confirming a desired proportion of bicarbonate concentrate and acid concentrate components in dialysate, the bicarbonate concentrate including bicarbonate ions and the acid concentrate including glucose, said test strip comprising:
   a first medium capable of indicating a concentration of bicarbonate ion in the dialysate; and
   a second medium capable of indicating a concentration of glucose in the dialysate.

2. The test strip of claim 1, wherein said first medium is impregnated within and localized at a first region of said test strip, said second medium is impregnated within and localized at a second region of said test strip, and said first region and said second region being slightly separated.

3. The test strip of claim 1, wherein the concentration of bicarbonate ion in the dialysate is in the range of about 15 to about 70 mEq/L.

4. The test strip of claim 1, wherein the concentration of bicarbonate ion in the dialysate is in the range of 33 to 37 mEq/L.

5. The test strip of claim 1, wherein the concentration of glucose in the dialysate is in the range of 0 to 5 g/L.

6. The test strip of claim 1, wherein the concentration of glucose in the dialysate is about 2.0 g/L.

7. The test strip of claim 1, wherein said first medium includes an acid and a chromogenic pH indicator.

8. The test strip of claim 7, wherein said acid has a pKa of about 2.9 to about 5.6.

9. The test strip of claim 7, wherein said acid is selected from the group consisting of citric acid, succinic acid, tartaric acid, phthalic acid, fumaric acid, and gluconic acid.

10. The test strip of claim 7, wherein said chromogenic pH indicator has a pKa value of about 3.8 to about 7.6.

11. The test strip of claim 7, wherein said chromogenic pH indicator is selected from the group consisting of bromophenol blue, methyl orange, tetrabromophenol blue, congo red, bromocresol green, litmus, and phenol red.

12. The test strip of claim 1, wherein said first medium further includes an inert dye.

13. The test strip of claim 1, wherein said second medium includes a glucose oxidase enzyme, a peroxidase enzyme, and a chromogenic oxidation/reduction indicator.

14. The test strip of claim 13, wherein said chromogenic oxidation/reduction indicator is selected from the group consisting of o-dianisidine, 4-AAP/phenol, MBTH/3-dimethylaminobenzoic acid, tetramethyl benzidine, and potassium iodide.

15. The test strip of claim 1, wherein said second medium further includes an inert dye.

16. The test strip of claim 1 further comprising a third medium capable of indicating the pH of a dialysate.

17. The test strip of claim 16, wherein said third medium is impregnated within and localized at a third region of said test strip.

18. The test strip of claim 16, wherein the pH of the dialysate is in the range of about 6 to about 8.5.

19. The test strip of claim 16, wherein the pH of the dialysate is about 7.0.

20. The test strip of claim 16, wherein said third medium includes a pH indicator.

21. The test strip of claim 20, wherein said pH indicator has a pKa value of about 6.8 to about 7.9.

22. The test strip of claim 20, wherein said pH indicator has a pKa value of 7.0.

23. The test strip of claim 20, wherein said pH indicator is selected from the group consisting of bromothymol blue, pyrocatechol violet, tetra-bromophenol sulfonephthalein, neutral red, phenol red, cresol red, and metacresol purple.

24. A test strip for confirming a desired proportion of components in dialysate, the components including bicarbonate concentrate and acid concentrate, the bicarbonate concentrate having bicarbonate ions and the acid concentrate having glucose, the test strip comprising:
   a first region having a bicarbonate test pad mounted thereon, said bicarbonate test pad being impregnated with a first medium capable of indicating a concentration of bicarbonate ion in the dialysate;
   a second region having a glucose test pad mounted thereon, said glucose test pad being impregnated with a second medium capable of indicating a concentration of glucose in the dialysate; and
   a strip of backing material.

25. The test strip of claim 24, wherein the concentration of bicarbonate ion in the dialysate is in the range of about 15 to about 70 mEq/L.

26. The test strip of claim 24, wherein the concentration of bicarbonate ion in the dialysate is in the range of 33 to 37 mEq/L.

27. The test strip of claim 24, wherein the concentration of glucose in the dialysate is in the range of 0 to 5 g/L.

28. The test strip of claim 24, wherein the concentration of glucose in the dialysate is about 2.0 g/L.

29. The test strip of claim 24, wherein said first medium includes an acid and a chromogenic pH indicator.

30. The test strip of claim 29, wherein said acid has a pKa of about 2.9 to about 5.6.

31. The test strip of claim 29, wherein said acid is selected from the group consisting of citric acid, succinic acid, tartaric acid, phthalic acid, fumaric acid, and gluconic acid.

32. The test strip of claim 31, wherein said chromogenic pH indicator has a pKa value of about 3.8 to about 7.6.

33. The test strip of claim 29, wherein said chromogenic pH indicator is selected from the group consisting of bromophenol blue, methyl orange, tetrabromophenol blue, congo red, bromocresol green, litmus, and phenol red.

34. The test strip of claim 24, wherein said first medium further includes an inert dye.

35. The test strip of claim 24, wherein said second medium includes a glucose oxidase enzyme, a peroxidase enzyme, and a chromogenic oxidation/reduction indicator.

36. The test strip of claim 35, wherein said chromogenic oxidation/reduction indicator is selected from the group consisting of o-dianisidine, 4-AAP/phenol, MBTH/3-dimethylaminobenzoic acid, tetramethyl benzidine, and potassium iodide.

37. The test strip of claim 24, wherein said second medium further includes an inert dye.

38. The test strip of claim 24 further comprising a third region having a pH pad mounted thereon, said pH pad being impregnated with a third medium capable of indicating a pH of the dialysate.

39. The test strip of claim 38, wherein the pH of the dialysate is in the range of about 6 to about 8.5.

40. The test strip of claim 38, wherein the pH of the dialysate is about 7.0.

41. The test strip of claim 38, wherein said third medium includes a pH indicator.

42. The test strip of claim 38, wherein said pH indicator has a pKa value of about 6.8 to about 7.9.

43. The test strip of claim 38, wherein said pH indicator has a pKa value of 7.0.

44. The test strip of claim 38, wherein said pH indicator is selected from the group consisting of bromothymol blue, pyrocatechol violet, tetra-bromophenol sulfonephthalein, neutral red, phenol red, cresol red, and metacresol purple.

* * * * *